Figure 1:
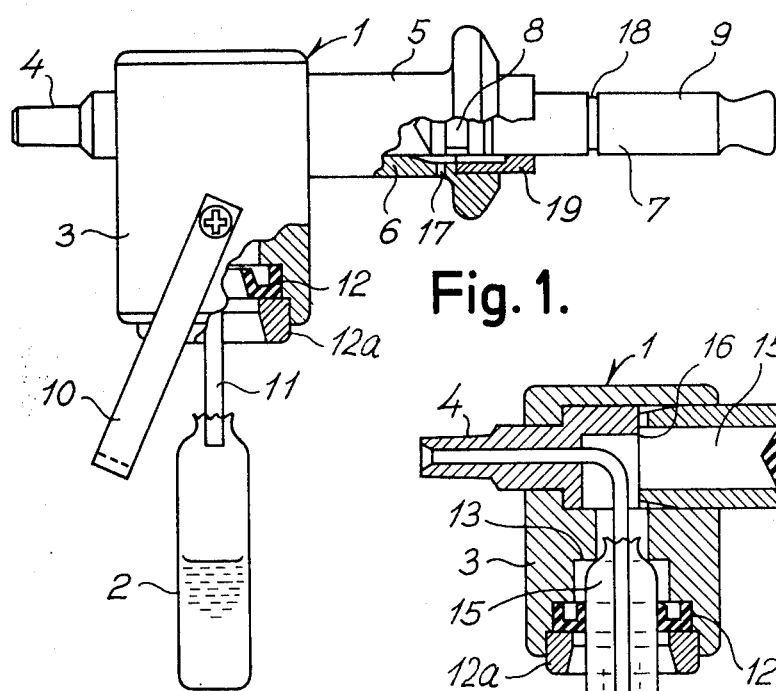

United States Patent [19]

Andersen et al.

[11] 4,275,774
[45] Jun. 30, 1981

[54] METHOD AND AN APPARATUS FOR TRANSFERRING A REFERENCE LIQUID FROM AN AMPOULE TO AN ELECTROCHEMICAL MEASURING INSTRUMENT

[76] Inventors: Jørgen Andersen, Dyrespringvej 3, DK-2730 Herlev; Ib Reimer-Nielsen, Solkaer 23, DK-2610 Rødovre, both of Denmark

[21] Appl. No.: 11,947

[22] Filed: Feb. 13, 1979

[30] Foreign Application Priority Data

Sep. 7, 1978 [DK] Denmark .................. 3966/78

[51] Int. Cl.³ .......................................... B65B 3/04
[52] U.S. Cl. ...................................... 141/1; 222/325; 222/394
[58] Field of Search ........... 141/329, 330, 19, 250–284, 141/129, 130, 1–12, 98; 222/325, 394

[56] References Cited

U.S. PATENT DOCUMENTS

| 3,843,326 | 10/1974 | Lichtenstenen | 141/329 |
| 3,885,414 | 5/1975 | Reville | 73/1 R |

FOREIGN PATENT DOCUMENTS

| 558949 | 9/1932 | Fed. Rep. of Germany | 141/329 |
| 537374 | 6/1941 | United Kingdom . | |
| 626964 | 7/1949 | United Kingdom . | |
| 888906 | 2/1962 | United Kingdom . | |
| 1321975 | 7/1973 | United Kingdom . | |
| 1384443 | 2/1975 | United Kingdom . | |
| 1435374 | 5/1976 | United Kingdom . | |

Primary Examiner—Houston S. Bell, Jr.
Attorney, Agent, or Firm—Hubbell, Cohen, Stiefel & Gross

[57] ABSTRACT

Ampoule-packed reference liquids for electrochemical measuring instruments, especially blood measuring instruments, are transferred from the ampoule to the measuring instrument pneumatically by providing a discharge conduit from the liquid in the ampoule, and providing, at the surface of the liquid in the ampoule, an elevated pressure so as to discharge liquid from the ampoule through the said conduit, and introducing the liquid in the measuring instrument. This pneumatic way of transfer is shown to give less distortion of the data of the reference liquid and to be less operator-dependent than the known methods. Invention also concerns a dispenser for performing the method, typically comprising an adaptor for receiving an opened ampoule and a pump for establishing the elevated pressure.

11 Claims, 9 Drawing Figures

U.S. Patent Jun. 30, 1981 Sheet 3 of 3 4,275,774
Fig. 8.
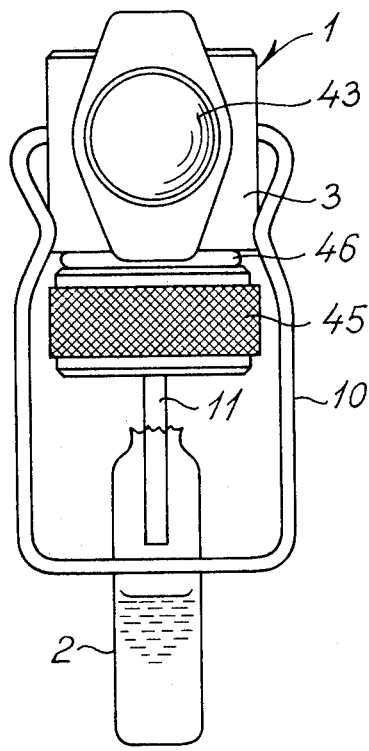
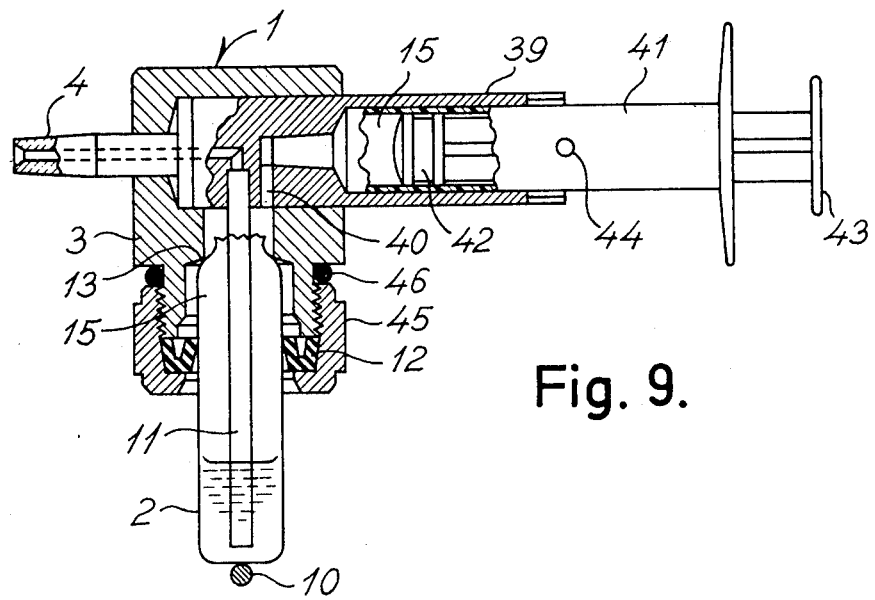
Fig. 9.

METHOD AND AN APPARATUS FOR TRANSFERRING A REFERENCE LIQUID FROM AN AMPOULE TO AN ELECTROCHEMICAL MEASURING INSTRUMENT

The present invention concerns a method for transferring a reference liquid from an ampoule to an electrochemical measuring instrument, and an apparatus for use in the method.

Various precision measuring instruments measuring various parameters on liquid samples, for example pH measuring instruments and blood measuring equipment for determination of one or more of the parameters hemoglobin content, oxygen saturation, pH, $Pco_2$ and $Po_2$ in blood samples, are adapted to be calibrated or controlled with respect to the quality of their measurement and operation by means of precision-made, ampoule-packed reference liquids with known and/or fixed values for the parameter or parameters measured by the instrument. With suitable, predetermined intervals, one or more sequential reference liquids of this kind are introduced in the instrument instead of liquid samples, and the measuring results of the instruments on the reference liquid or liquids or the deviation between the measuring results on two sequentially introduced portions of reference liquid is or are recorded and used for checking the function of the instrument and/or for calibrating the instrument.

Especially the reliability of blood measuring equipment used, for example, in hospitals may be of critical importance in the clinical situation, and in several countries, the authorities therefore aim at giving exact prescriptions for in which manner and how frequently blood measuring equipment is to be subjected to quality control with respect to their function and operation and/or to calibration.

The transfer of reference liquids from ampoules to measuring instruments is therefore a procedure which is daily performed in a very large number over the world, and the performance of which is directly decisive to the reliability of the measurements performed with the instruments in question. The commonly used methods for transferring a reference liquid from an ampoule to an electrochemical measuring instrument subsequent to opening the ampoule are:

(1) A syringe is equipped with a needle, the content of the ampoule is suctioned into the syringe through the needle, the needle is dismounted, and while the syringe is held with the needle mounting cone pointing upward, one knocks gently on the syringe so that the air volume which is almost inevitably formed in the suctioning operation, collects at the top, the air volume is removed by moving the piston a little in upward direction, and thereafter the necessary volume of reference liquid is sprayed into the measuring instrument.

(2) The contents of the ampoule are suctioned into a syringe, but without using any needle, the needle mounting cone of the syringe being introduced in the ampoule, and the ampoule being held in the necessary angle for this. Thereafter, one proceeds as described under (1) with respect to removing any air bubbles and spraying into the instrument.

(3) The ampoule is turned upside down and held over the inlet of the instrument so that this is covered by the liquid, and the liquid is suctioned into the instrument through the aspiration procedure of the instrument.

(4) On the inlet of the instrument, a short tube is applied, the other end of the tube is immersed in the ampoule, and the reference liquid is transferred into the instrument through the aspiration procedure of the instrument.

However, all of these methods suffer from considerable disadvantages. The methods (1), (2) and (4) require exchange of the needle and the syringe or the tube when changing between the 2-3 reference liquids which are ordinarily necessary and each of which represents one level of the parameter or parameters in question, or alternatively to this exchange, careful washing in methods (1) and (2) (however, this washing in itself, of course, incurs a considerable risk for dilution of the sample with consequent destruction of its parameter values). Apart from this, methods (1) and (2) are cumbersome and relatively time-consuming. Method (3) must be rejected on grounds of principle, as experience shows that in some cases, air will unintentionally be entrained when suctioning. Such air will give rise to distortion of the results, and it is not possible to ascertain in advance whether air has been suctioned in or not, which means that it is only the measuring result obtained which will indicate this, and such situation does not fulfill the requirements to a quality control or calibration.

In addition, the methods (1), (2) and (4) require that the personnel performing the quality control or calibration is well instructed and remembers to perform exchange of needle, syringe and tube (or the careful washing of needle or tube) at each new operation.

At the same time, the field in which quality control and calibration is of perhaps the most critical importance, that is, the blood measuring field, is also the field in which the known methods for transferring reference liquids from ampoules to the measuring instruments are most problematic. For calibration of blood measuring equipment which determines blood pH, $Pco_2$ and/or $Po_2$, reference liquids are used which are precision-made for an exact particular partial pressure of $Pco_2$ and/or $Po_2$, and which ideally are to be transferred to the measuring apparatus without change of these parameters. In the known methods for transferring a reference liquid to a blood measuring equipment, one is, however, often very far from the ideal. As mentioned above, method (3) must be rejected, as this method may incur even very considerable errors through entrained air, without the operator having had any possibility of knowing that such entrainment of air has taken place. The results in method (1) are very dependent on the manual performance, and therefore very dependent on the person who performs the method, as it is difficult to standardize the suctioning rate. A high suctioning rate requires a high vacuum in the syringe and therefore always incurs the risk that microbubbles will be formed, that is, that the dissolved gasses will be withdrawn from the liquid. Once microbubbles have been formed, they will have no tendency to redissolve, and even the formation of very small amounts of microbubbles may completely destroy the exactitude of the reference liquid. On the other hand, when these methods are used, there is contact between the reference liquid and a certain (although small) air volume (dead volume) in the syringe, and this contact may also result in a certain change of the $Po_2$ and $Pco_2$ partial pressures. If the suctioning is erroneously continued for a too long period, air will be directly suctioned into the syringe. In methods (1) and (2), the liquid contacts large new areas in the syringe), and this increases the risk of contamination of the liquid.

Therefore, there is a need for a suitable, in principle correct, simple method for transferring a reference liquid from an ampoule to a measuring instrument, which method is independent of the person who performs it with respect to the results obtained and their reproducibility. The present invention provides a method which fulfills these requirements.

The method according to the invention for transferring a reference liquid from a reference liquid-containing ampoule to an electrochemical measuring instrument comprises (a) opening said ampoule, (b) providing a discharge conduit having an inlet and an outlet and extending through the opening of the ampoule into the inner space thereof so as to position said inlet below the surface of the liquid in said ampoule, (c) providing, at the surface of the liquid in said ampoule, a gas pressure exceeding the gas pressure at the outlet of the conduit so as to discharge liquid from the ampoule through said outlet and communicating the outlet with said measuring instrument so as to introduce reference liquid into said instrument, (d) terminating the liquid introduction into the measuring instrument while the inlet of the conduit is still located below the surface of the reference liquid in the ampoule.

The method according to the invention is suitably performed by means of a simple apparatus which also constitutes part of the present invention and which can be defined as an apparatus for transferring a reference liquid from a reference liquid-containing ampoule in which an opening has been provided, to an electrochemical measuring instrument, said apparatus comprising (a) a body member defining a cavity therein, (b) annular sealing means mounted on said body member and defining an orifice communicating with said cavity, said sealing means being adapted to sealingly engage with the surface of the ampoule so as to communicate the inner space thereof with said cavity, (c) a liquid discharge conduit having an inlet end portion extending outwardly from said body member, through said orifice and beyond said sealing means so as to extend into the inner space of the ampoule when engaged with said sealing means, and an outlet end adapted to communicate with said measuring instrument, (d) gas pressure increasing means for increasing the gas pressure in said cavity when said sealing means are in engagement with said ampoule, so as to discharge liquid from said ampoule through the conduit outlet end.

Although any means for controllably increasing the pressure could be used, it is preferred to use, as the pressure increasing means, a cylinder communicating with the cavity and a piston displaceably mounted in said cylinder. The method of the invention may then be performed by placing the opened ampoule in the apparatus into engagement with the annular sealing means, connecting the outlet end of the liquid conduit with the inlet of the measuring instrument, and activating the piston.

The liquid conduit of the apparatus, which in the following will be designated the "dispenser" may, prior to being communicated with the liquid inlet of the measuring instrument, be emptied for air by allowing part of the reference liquid to pass up to the outlet end of the conduit, and a washing/cleaning of the conduit may be performed by allowing a suitable forerun of the reference liquid to pass out through the outlet prior to establishing the communication with the inlet of the measuring instrument. However, measuring instruments exist, for example the blood gas measuring equipment Radiometer ABL 2 mentioned below, which in their measuring procedure only use the last portion of an injected volume of reference liquid which may, in principle, be arbitrarily large, and in connection with such measuring instruments, the initial removal of air and washing is superfluous, provided that a sufficient volume of reference liquid is supplied.

The method of the invention avoids the cumbersome use of syringes and needles, and makes it unnecessary for the operator to use—and remember to change—a tube like in method (4). The risk of introduction of air bubbles in the measuring instrument is eliminated, and in the field of blood measuring instruments, the method of the invention ideally fulfils all requirements: there is no risk of contamination by contact with large new areas, and as the transfer from the ampoule to the measuring instrument involves no suctioning, there is no longer the risk of formation of microbubbles which in the known methods reduce the exactitude of the measuring results and make the measuring results dependent on the variation in the manual performance. It has surprisingly been found that the method of the invention can be used with optimum result for anaerobic transfer of reference liquids to the pH, $P_{CO_2}$ and/or $P_{O_2}$ part of blood measuring equipment, even though the transfer of the reference liquid in the method of the invention is preferably performed using air as the gas dose which when introduced causes the liquid to be transferred. In other words, this transfer, which must necessarily be anaerobic, can be optimally performed using exactly air as transport medium, without distortion of the parameters of the reference liquid due to the contact with the transport air. The improvements obtained in this regard in relation to known methods are clearly documented in the below comparison tests. The explanation of this surprising improvement of the anaerobic transfer using air as transport medium is probably to be found in the fact that while the air will to a certain degree equilibrate with the surface of the liquid in the ampoule, there will be practically no equilibration between the liquid surface and the lower liquid layers in the ampoule which are transferred to the measuring instrument by the method of the invention.

Comparison Tests

The above-mentioned known methods and the method of the invention were compared by transferring a reference liquid from an ampoule to a blood measuring instrument, Radiometer ABL 2, which is a self-calibrating automatic blood measuring apparatus which, inter alia, determines pH, $P_{CO_2}$ and $P_{O_2}$ on a blood sample.

The transfer was performed according to the following methods:

(1) The contents of the ampoule were suctioned into a dispensable plastic syringe through a needle applied on the syringe. The syringe was turned upside down, the needle was removed, any air bubbles were collected at the top by slightly knocking at the syringe and were removed through a minor advance of the piston, whereafter 1 ml of the reference liquid was sprayed into the measuring instrument.

(2) The reference liquid was suctioned from the ampoule into the syringe without using a needle. In all other respects, the method was as described under (1).

(3) The opened ampoule was held upside down over the inlet of the instrument in such a way that the inlet was covered by liquid. The aspiration of the instrument was activated until the instrument's "sample" lamp alighted, indicating that the necessary liquid volume had been introduced in the instrument.

(4) A 5 cm PVC tube was applied on the inlet of the instrument. The ampoule was arranged so that the other end of the tube reached the bottom of the ampoule, whereafter the aspiration function of the instrument was activated until the "sample" lamp alighted.

(5) About 1 ml reference liquid was sprayed into the instrument by means of the dispenser described below and shown in FIGS. 1 and 2, the outlet member 4 of the dispenser being placed around the inlet of the instrument, and the end of the outlet member 4 being pressed against the washer surrounding the inlet of the instrument.

All the experiments were performed with one and the same reference liquid (a bicarbonate phosphate buffer solution equilibrated with carbon dioxide and oxygen). A reference liquid was selected in which the $CO_2$ level is high and the $O_2$ level low, considering that any contamination from contact with the air will lower $P_{CO_2}$ and raise $P_{O_2}$.

The result of the experiments appear from the below table in which the stated measuring values for each method are mean values for 10 measurements divided on two instruments:

TABLE 1.

| Method | 1 | 2 | 3 | 4 | 5 |
|---|---|---|---|---|---|
| pH | 7.126 | 7.126 | 7.123 | 7.125 | 7.126 |
| $P_{CO_2}$ (mm Hg) | 59.2 | 59.8 | 57.2 | 55.9 | 59.9 |
| $P_{O_2}$ (mm Hg) | 60.0 | 59.5 | 62.7 | 66.4 | 57.7 |

The standard deviation on the individual measurements did not show substantial differences between the five methods; however, in method 3, there were some cases where entrained air caused deviating results, confer what has been stated above concerning the basically unacceptable character of method 3.

A comparison between the levels obtained shows that method 5, that is, the method of the invention, is clearly the one giving by far the best results.

While the results stated above were obtained by a trained operator, another comparison test was performed by two untrained operators after a brief instruction. Again, the ampoules used contained reference liquid with low $O_2$ level. The measurements were performed in "rounds" in such a way that for each method, each operator transferred liquid from an ampoule to a first blood measuring instrument (Radiometer ABL 1), whereafter the same procedure was repeated for a second Radiometer ABL 1 instrument. Each operator performed 3-4 measuring rounds. The operator measured on reference liquids of the same batch. Mean values and deviation were calculated for each person for each apparatus and each method. Mean values and deviations for the two instruments were thereafter combined to the results shown in the below table 2. No data were disregarded. In order to assess operator-conditioned deviations, $\Delta$ = measurement $_{operator\ 2}$ − measurement $_{operator\ 1}$ was calculated for each of the 5 methods and stated in table 3.

The methods referred to in table 2 are same as methods 1-5 described above. It is evident from the tables that method 5 showed both the lowest deviation and the smallest difference between the two operators.

| | pH | | | $P_{CO_2}$ | | | $P_{O_2}$ | | | |
|---|---|---|---|---|---|---|---|---|---|---|
| Method No. | $\bar{x}$ pH | $s_0$ mpH | Number of measurements | $\bar{x}$ mm Hg | $s_0$ mm Hg | Number of measurements | $\bar{x}$ mm Hg | $s_0$ mm Hg | Number of measurements | Operator No. |
| 1 | 7.142 | 1.4 | 8 | 55.8 | 0.59 | 8 | 66.6 | 3.4 | 8 | |
| 2 | 7.144 | 2.5 | 8 | 55.6 | 0.66 | 8 | 74.4 | 4.2 | 8 | |
| 3 | 7.139 | 2.8 | 6 | 55.0 | 0.54 | 6 | 67.4 | 6.1 | 6 | 1 |
| 4 | 7.138 | 1.3 | 6 | 53.4 | 3.9 | 6 | 64.5 | 2.6 | 6 | |
| 5 | 7.139 | 0.6 | 6 | 57.0 | 0.32 | 6 | 55.4 | 0.71 | 6 | |
| 1 | 7.144 | 5.7 | 7 | 52.5 | 8.0 | 7 | 85.8 | 25 | 7 | |
| 2 | 7.148 | 16 | 7 | 54.2 | 4.7 | 7 | 82.0 | 21 | 7 | |
| 3 | 7.137 | 1.1 | 6 | 56.0 | 0.56 | 6 | 59.0 | 0.65 | 6 | 2 |
| 4 | 7.137 | 1.1 | 6 | 56.0 | 0.72 | 6 | 59.9 | 2.1 | 6 | |
| 5 | 7.137 | 0.71 | 7 | 57.2 | 0.69 | 7 | 53.0 | 0.85 | 7 | |

TABLE 3.

| Method | $\Delta$ millipH | $\Delta$ $P_{CO_2}$, mm Hg | $\Delta$ $P_{O_2}$, mm Hg |
|---|---|---|---|
| 1 | 2 | −3.3 | 19.2 |
| 2 | 4 | −1.4 | 7.6 |
| 3 | −2 | 1.0 | −8.4 |
| 4 | −1 | 2.6 | −4.5 |
| 5 | −2 | +0.2 | −2.4 |

Figure 2:
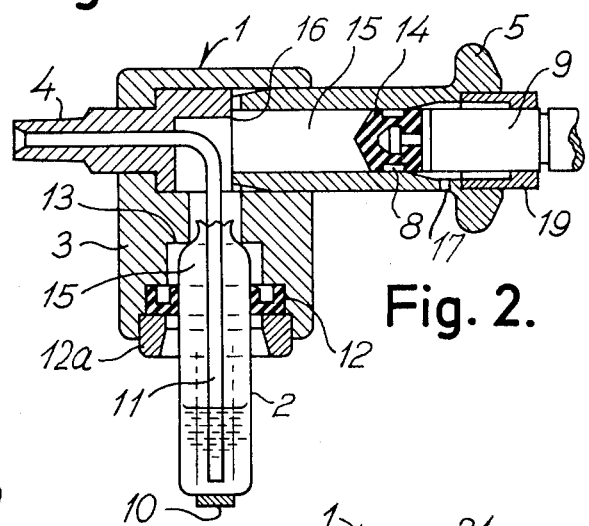
Figure 3:
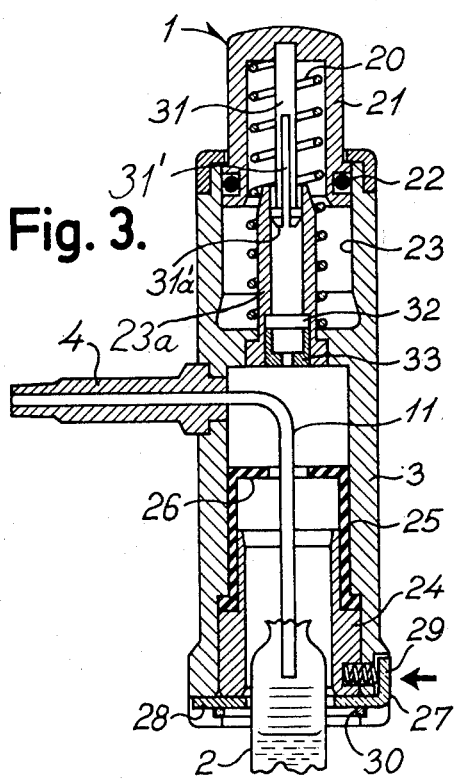
Figure 4:
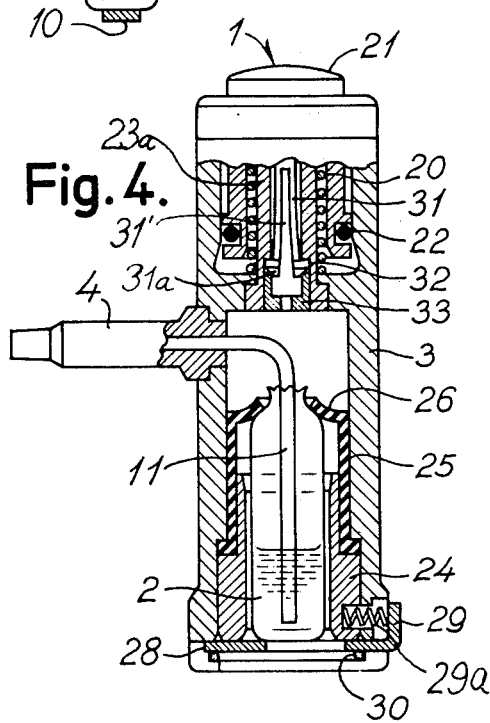
Figure 5:
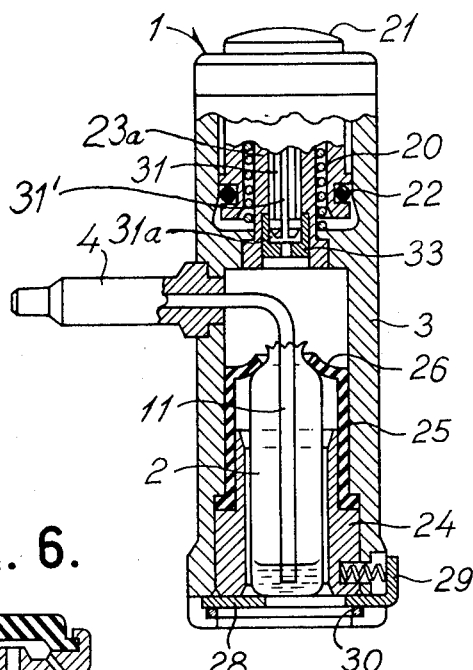
Figure 6:
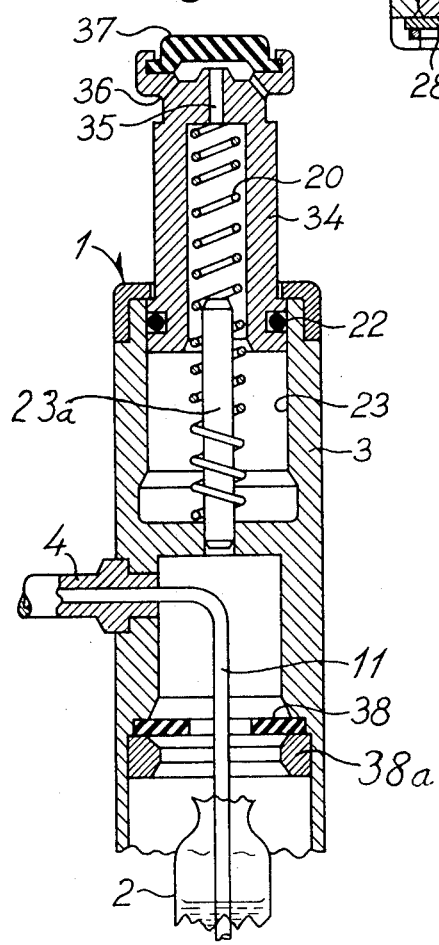
Figure 7:
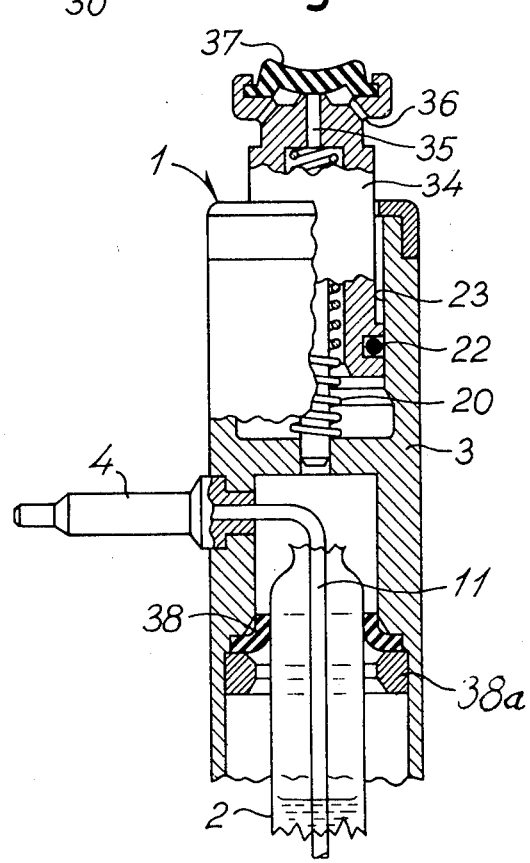

The invention is now described in greater detail with reference to the drawing in which FIG. 1 is a side view and partially sectional view showing a first embodiment of a dispenser apparatus according to the invention, FIG. 2 is a sectional view of the dispenser shown in FIG. 1, FIG. 3 is a sectional view of a second embodiment of a dispenser according to the invention, illustrating a first step of operation, FIG. 4 is a side view and partially sectional view of the dispenser shown in FIG. 3, illustrating a second step of operation, FIG. 5 is a side view and partially sectional view of the dispenser shown in FIG. 3, illustrating a third step of operation, FIG. 6 is a sectional view of part of a third embodiment of the dispenser or apparatus according to the invention, illustrating a first step of operation, FIG. 7 is a side view and partially sectional view of part of the dispenser shown in FIG. 6, illustrating a second step of operation, FIG. 8 is an end view of a fourth embodiment of the apparatus or dispenser according to the invention, and FIG. 9 is a side view and partially sectional view of the dispenser shown in FIG. 8.

FIGS. 1 and 2 show a discharging apparatus or dispenser 1 for discharging a reference liquid from an ampoule 2. The apparatus or dispenser comprises a housing or body member 3, having a passage or bore for receiving the ampoule. The dispenser also comprises a syringe or piston pump 5 including a cylinder 6 and a piston member 7. The piston member 7 comprises a piston 8 which is preferably made from rubber or plastic, and a piston rod 9. The pump 5 is mounted in the housing 3 so that the inner space of the cylinder 6 communicates with the ampoule receiving passage of the housing. An outlet member 4 is mounted in the housing 3 substantially coaxial to the cylinder 6 and extends from the housing as shown in FIG. 2. A discharge conduit or tube 11 has an outlet end mounted in said outlet member, and an inlet end extending axially through the ampoule receiving passage as shown in FIG. 2. A strap-shaped ampoule supporting member 10 is pivotally mounted on the body member 3 as shown in FIG. 1.

When reference liquid is to be discharged from an ampoule 2, the ampoule is opened and the open end is inserted into the ampoule receiving passage of the housing, whereby the inlet end of the discharge conduit 11 is inserted through the opened end of the ampoule 2 as shown in FIG. 1 and dipped into the reference liquid contained in the ampoule. An annular sealing member 12 mounted in the housing 3 at the entrance of the ampoule receiving passage engages sealingly with the outer cylindrical surface of the ampoule 2. The sealing member 12, which is preferably channel shaped and made from rubber or plastic, is retained in position by means of a mounting ring 12a. The ampoule 2 may be pushed into the ampoule receiving passage till the shoulder of the ampoule engages with an abutment surface 13 formed within the housing 3. The supporting member 10 may now be tilted from the position shown in FIG. 1 to that shown in FIG. 2 in which the ampoule is retained in its inserted position. When the piston 8 is in a retracted position with a front sealing lip 14 tightly engaging the inner surface of the cylinder 6, the inner surfaces of the cylinder 6, the housing 3, and the ampoule 2 define an inner space 15 which is substantially air-tightly sealed in relation to the ambient atmosphere. When the piston 8 is advanced, the pressure in the space 15 is increased whereby the liquid in the ampoule 2 will be pressed through the discharge conduit 11 and out through the outlet member 4 which may be communicating with an electrochemical measuring device or instrument which is to be calibrated or subjected to quality control.

The outlet member 4 may have any shape suitable for communicating it with the reference liquid inlet of the measuring device to be calibrated. By way of examples, the outer surface of the projecting part of the outlet member 4 may be cylindrical or shaped as a standard cone, such as a Luer cone or a Record cone.

The inlet end of the discharge conduit 11 has such a length that the free end thereof is located almost at the bottom of the ampoule 2 when the ampoule is in its engaged position as shown in FIG. 2. The innermost position of the piston 8 is defined by the inner end surface of the outlet member 4 defining a stop surface 16. The maximum effective stroke of the piston 8 should be selected so that it provides a pressure increase within the space 15 which on the one hand is sufficient to expel the desired amount of reference liquid from the ampoule 2, and on the other hand insufficient to expel such an amount of reference liquid that the liquid surface in the ampoule sinks to the level of the lower free end of the discharge conduit 11. The conduit 11 may form an integral tube section as shown or be made from a plurality of interconnected tube sections. The conduit 11 may typically have an inner diameter within the range from a few millimeters to a capillary tube diameter, for example 0.3 mm. When the conduit has a small diameter, for example a capillary tube diameter, it will provide such a resistance against liquid flow therethrough that this results in a controlled slow delivery of the reference liquid from the dispenser. When the desired amount of reference liquid has been transferred from the ampoule 2 to an electrochemical measuring instrument, the dispenser is disconnected from the measuring instrument and the piston is moved to its retracted position in a cylinder part of an increased inner diameter in which the piston 8 does not sealingly engage with the inner wall of the cylinder 6 whereby the space 15 communicates with the ambient atmosphere through a hole 17 in the cylinder wall. The ampoule 2 from which reference liquid has been discharged may now be removed from the dispenser, and another ampoule may be inserted, if desired. The piston rod is advantageously provided with an annular groove 18 or another marking indicating the proper position of the piston before communicating the outlet member 4 with the measuring instrument. Displacement of the piston from its most retracted position to a position in which the groove 18 registers with the front end surface of a sleeve 19 causes that a small amount of reference liquid is expelled serving as a forerun flushing the conduit 11 and the bore of the outlet member 4.

Reference is now made to FIGS. 3–5 in which like parts are indicated by like reference numbers. The dispenser shown in FIGS. 3–5 comprises a pump having a piston 21 biased towards its retracted position by means of a coiled spring 20. The piston includes a sealing ring or a O-ring 22 which is in sealing engagement with the inner wall 23 of an upper bore in the housing 3 forming the cylinder of the pump. A cup-shaped sealing member 25 forming an annular flange 26 defining a central opening is mounted within the ampoule receiving bore of the housing 3 by means of a retaining sleeve 24. When an opened ampoule 2 is inserted into the sleeve 24, sufficient clearance is provided between the outer wall of the ampoule and the inner wall of the sleeve to allow air to escape so as to avoid any building up of pressure. When the shoulder of the ampoule 2 has been engaged with the flange 26 of the sealing member 25 as shown in FIG. 4, the ampoule may be retained in that position by means of a supporting member 28. The supporting member 28 is shaped as a ring mounted rotatably around an axis or set in relation to the axis of the sleeve 24. The supporting member 28 is provided with an up-turned flange or projection 29 biased by a spring 29a mounted in a bore in the sleeve 24. Furthermore, the supporting member 28 is retained in position by means of a resilient locking ring 30.

Before an ampoule 2 is inserted in the housing 3 as shown in FIG. 3 the supporting member 28 is rotated to a position in which the opening thereof registers with the bore on the sleeve 24. When the ampoule has been inserted so that the shoulder thereof sealingly engages with the flange 26, the supporting member 28 is rotated to a position in which the opening therein is offset in relation to the bore of the sleeve 24 so that part of the supporting member engages with the bottom surface of the ampoule 2 for retaining the ampoule in position. In the embodiment of the dispenser shown in FIGS. 3-5 the pump is provided with means for locking the piston 21 in its depressed position. The cup-shaped piston 21 receives the upper end of the spring 20, the lower end of which surrounds a tube member 23a extending axially into the cylinder 23. The piston locking means comprise a locking pin 31 mounted on the piston 21 and extending axially into the tube member 23a, and an enlarged section 32 of the inner bore of the tube member 23a. At its free end the locking pin 31 is provided with an enlarged head 31a, and the free end portion of the locking pin 31 is provided with an axially extending slot 31'. The locking pin 31 is made from a resilient material such as plastic, and the parts of the head 31a are biased radially outwardly. When the piston 21 is depressed against the action of the spring 20, the locking pin 31 is displaced in relation to the tube member 23a till the head 31a of the pin is brought into engagement with the enlarged section 32 as shown in FIG. 4. Thereby the piston 21 is locked in its depressed position. Depression of the piston 21 causes an increase of gas pressure in the inner space of the housing 3 above the flange 26 and, consequently, also in the inner space of the ampoule 2. The increased air pressure in the ampoule 2 initiates discharge of reference liquid through the discharge conduit 11 as previously described, and in the present embodiment the conduit 11 is preferably a capillary tube offering a relatively high resistance to liquid flow therethrough so that liquid will be discharged at a relatively low and uniform flow rate even when the piston 21 is depressed rather quickly. The maximum stroke of the piston 21 is selected so that the increase of air pressure caused within the inner space of the ampoule is sufficient to discharge the desired amount of the liquid from the ampoule 2 as previously explained.

When the desired amount of liquid has been discharged from the ampoule 2, the piston 21 is released and returned to its starting position by means of the spring 20. Release of the piston 21 may be obtained by further depressing the piston towards the lower end of the cylinder 23, whereby possible overpressure in the cylinder will be released because the sealing ring 22 comes into non-sealing engagement with a cylinder wall section of increased diameter. The said further depression of the piston 21 also causes movement of the head 31a of the locking pin 31 towards a release member 33 displaceably mounted within the enlarged section 32 of the inner bore of the tube member 23a. The upper edge of the release member 33 will then cooperate with the tapered head 31a and comprise the same radially so that the head is received within the release member. When depression of the piston 21 is released, the piston will be moved upwardly under the bias of the spring 20. The release member 33 will then also be moved upwardly together with the head 31a till the release member engages a shoulder or stub surface in the bore of the tube member 23a as shown in FIG. 4. Thereafter, the piston 21 will continue its movement to its starting position shown in FIG. 3. When the used ampoule 2 is to be removed from the dispenser 1, the supporting or retaining member 28 is rotated to the position shown in FIG. 3 in which the opening therein registers with the bore of the retaining sleeve 24. The ampoule may now be expelled from the dispenser by slightly depressing the piston 21 so as to create a slight overpressure within the housing 3.

FIGS. 6 and 7 show a third embodiment of the apparatus according to the invention which is similar to that shown in FIGS. 3-5, and wherein similar parts are indicated by similar reference numerals. In FIGS. 6 and 7 the cupshaped sealing member shown in FIGS. 3-5 has been replaced by a flat annular sealing member 38 mounted in the housing 3 by means of a mounting ring 38a. A piston 34 corresponds to the piston 31 shown in FIGS. 3-5 apart from a valve device arranged at the upper end of the piston 34. This valve device comprises a number of venting bores 36 and a resilient pressure button or member 37 of rubber or plastic covering the upper end surface of the piston 34 and defining together therewith a valve chamber 37a which is vented to the atmosphere by the venting bores 36. The valve chamber 37a is communicating with the cylinder 23 through a central bore 35. In the normal position of the button 37 shown in FIG. 6 the inner space of the cylinder 23 and of the housing 3 is communicating with the atmosphere through the tube member 23a, the central bore 35 and the venting bores 36. This fact secures that insertion of an ampoule 2 in the dispenseer does not create an overpressure within the housing 3. When, however, it is desired to discharge reference liquid from the ampoule by depressing the piston 34 as described above, the button 37 is activated by a finger pressure whereby it is deformed so as to close the upper end of the central bore 35 as shown in FIG. 7. Depression of the piston 34 will now create an overpressure in the ampoule 2 to expel reference liquid therefrom. When a suitable amount of liquid has been expelled or discharged, the button 37 is released, whereby it will return to its normal shape shown in FIG. 6. The overpressure in the cylinder 23 and the ampoule 2 will then be released through the bores 35 and 36, and the piston 34 will be returned to its starting position under the bias of the spring 20.

FIGS. 8 and 9 show a fourth and presently preferred embodiment of the dispenser or apparatus according to the invention. In principle, this embodiment substantially corresponds to the embodiments shown in FIGS. 1 and 2. In FIGS. 8 and 9 the pump has been replaced by a syringe which is preferably made from plastic. The cylinder 41 of the syringe is mounted in a mounting block 39 connected to the housing 3, and the outlet nozzle of the cylinder is communicating with the ampoule receiving bore of the housing by means of a transverse connecting bore 40 in the mounting block 39. A piston 42 formed integrally with a piston rod 43 is displaceably arranged within the cylinder 41 in a well-known manner. The sealing member 12 engaging with the outer surface of the ampoule 2 is mounted in the ampoule receiving bore of the housing by means of a screw cap 45 having a knurled outer surface part, and a sealing O-ring 46. The length of the effective stroke of the piston 42 is determined by the axial position of a bore 44 through the wall of the cylinder 41. The position of the bore 44 is, of course, chosen so that the desired amount of reference liquid is discharged from the ampoule when the piston 42 is moved to its innermost advanced position in the cylinder. The function of the embodiment shown in FIGS. 8 and 9 substantially corresponds to that described in connection with the embodiment of FIGS. 1 and 2.

For the most purposes it would be desirable to discharge a liquid volume from the ampoule in the order of 1–1.5 ml, and the total amount of reference liquid contained in the ampoule should, therefore, be adapted in relation thereto and may, for example, be about 2 ml. It should be understood that also when the method and apparatus of the present invention is used, the instructions and prescriptions given by the manufacturer of the reference should be carefully observed. For ampoule contained reference liquids for blood gas measuring instruments such instructions might, for example, comprise instructions as to careful thermostatic control of temperature and shaking of the ampoule content before use thereof.

We claim:

1. A method for transferring a reference liquid from a reference liquid-containing ampoule to an electrochemical measuring instrument comprising
   (a) opening said ampoule,
   (b) providing a discharge conduit having an inlet and an outlet and extending through the opening of the ampoule into the inner space thereof so as to position said inlet below the surface of the liquid in said ampoule,
   (c) providing, at the surface of the liquid in said ampoule, a gas pressure exceeding the gas pressure at the outlet of the conduit so as to discharge liquid from the ampoule through said outlet and communicating the outlet with said measuring instrument so as to introduce reference liquid into said instrument,
   (d) terminating the liquid introduction into the measuring instrument while the inlet of the conduit is still located below the surface of the reference liquid in the ampoule thereby substantially preventing the introduction of gas into said measuring instrument.

2. A method according to claim 1, wherein an initial amount of reference liquid is discharged through said conduit outlet prior to communicating the same with said measuring device.

3. A method according to claim 1, wherein the gas pressure in said ampoule is increased by reducing the volume of a chamber communicating therewith.

4. A method according to claim 1, wherein said reference liquid is used for calibration or quality control of an electrochemical blood measuring instrument.

5. A method according to claim 4, wherein the amount of liquid discharged from the ampoule is in the range of 1 to 1.5 ml.

6. A method according to claim 1, wherein the gas provided in said cavity is atmospheric air.

7. An apparatus for transferring a reference liquid from a liquid-containing ampoule in which an opening has been provided, to an electrochemical measuring instrument, said apparatus comprising
   (a) a body member defining a cavity therein,
   (b) annular sealing means mounted on said body member and defining an orifice communicating with said cavity, said sealing means being adapted to sealingly engage with the surface of the ampoule so as to communicate the inner space thereof with said cavity,
   (c) a liquid discharge conduit having an inlet end portion extending through said orifice and beyond said sealing means so as to extend into the inner space of the ampoule when engaged with said sealing means, and an outlet end adapted to communicate with said measuring instrument,
   (d) gas pressure increasing means for increasing the gas pressure in said cavity when said sealing means are in engagement with said ampoule, so as to discharge liquid from said ampoule through the conduit outlet end.

8. An apparatus according to claim 7, wherein said gas pressure increasing means comprise a cylinder communicating with said cavity and a piston displaceably mounted in said cylinder.

9. An apparatus according to claim 7, wherein said cavity is adapted to receive the upper end of the ampoule, said annular sealing means being adapted to engage with an outer cylindrical surface part of the ampoule.

10. An apparatus according to claim 7, further comprising means for retaining said ampoule in engagement with said sealing means.

11. An apparatus according to claim 10, wherein said retaining means comprise an ampoule supporting member pivotally mounted on said body member for engaging with the bottom portion of said ampoule.

* * * * *

UNITED STATES PATENT AND TRADEMARK OFFICE
CERTIFICATE OF CORRECTION

PATENT NO. : 4,275,774

DATED : June 30, 1981

INVENTOR(S) : ANDERSEN ET AL

It is certified that error appears in the above—identified patent and that said Letters Patent is hereby corrected as shown below:

Column 1, after line 5: Before the paragraph commencing with "The present invention", insert the heading:
--BACKGROUND OF THE INVENTION-- and thereunder the subheading
--Field of the Invention--.

Column 1, after line 10: Before the paragraph commencing with "Various precision", insert the subheading:
--Description of the Prior Art--.

Column 3, after line 29: Before the paragraph commencing with "The method according to", insert the heading:
--SUMMARY OF THE INVENTION--.

Column 6, after line 46: Before the paragraph commencing with "The invention is now", insert the heading:
--DESCRIPTION OF THE DRAWINGS--.

Column 12, in claim 7, line 30: Delete the "period (.)" and insert in place thereof the following:

UNITED STATES PATENT AND TRADEMARK OFFICE
CERTIFICATE OF CORRECTION

PATENT NO. : 4,275,774
DATED : June 30, 1981
INVENTOR(S) : ANDERSEN ET AL

It is certified that error appears in the above—identified patent and that said Letters Patent is hereby corrected as shown below:

--, said gas pressure increasing means and the position of the inlet end portion of said liquid discharge conduit being so interrelated that in the normal operation of the gas pressure increasing means, it increases the gas pressure in said cavity to such an extent that the amount of liquid discharged from said ampoule is of such an amount that the inlet of the conduit is still located below the surface of the reference liquid in the ampoule thereby substantially preventing the introduction of gas into said measuring instrument.--

Signed and Sealed this

Fifteenth Day of December 1981

[SEAL]

Attest:

Attesting Officer

GERALD J. MOSSINGHOFF

Commissioner of Patents and Trademarks